United States Patent
Gupta et al.

(10) Patent No.: US 9,440,928 B2
(45) Date of Patent: Sep. 13, 2016

(54) PROCESS FOR THE SYNTHESIS OF N-SUBSTITUTED CYCLIC ALKYLENE UREAS

(75) Inventors: Ram Gupta, Stamford, CT (US); Irina Kobylanska, Stamford, CT (US); Urvee Treasurer, Stamford, CT (US); Lawrence Flood, Norwalk, CT (US)

(73) Assignee: Allnex IP S.ar.L., Luxembourg (LU)

( * ) Notice: Subject to any disclaimer, the term of this patent is extended or adjusted under 35 U.S.C. 154(b) by 0 days.

(21) Appl. No.: 14/233,307

(22) PCT Filed: Jul. 19, 2012

(86) PCT No.: PCT/US2012/047310
§ 371 (c)(1),
(2), (4) Date: Feb. 14, 2014

(87) PCT Pub. No.: WO2013/012995
PCT Pub. Date: Jan. 24, 2013

(65) Prior Publication Data
US 2014/0179931 A1    Jun. 26, 2014

(30) Foreign Application Priority Data

Jul. 20, 2011    (EP) .................................. 11174655

(51) Int. Cl.
*C07D 233/34* (2006.01)
*C07D 233/36* (2006.01)
*C07D 233/32* (2006.01)

(52) U.S. Cl.
CPC ........... *C07D 233/36* (2013.01); *C07D 233/32* (2013.01); *C07D 233/34* (2013.01)

(58) Field of Classification Search
USPC .................................................... 548/323.5
See application file for complete search history.

(56) References Cited

U.S. PATENT DOCUMENTS

| | | | |
|---|---|---|---|
| 2,727,019 A | | 12/1955 | Melamed |
| 5,112,984 A | * | 5/1992 | Richey et al. ............. 548/323.5 |
| 7,186,828 B2 | * | 3/2007 | Guichard et al. ............. 540/492 |
| 7,645,855 B2 | * | 1/2010 | Bruchmann ........... C08G 71/02 528/370 |
| 7,935,819 B2 | * | 5/2011 | Halley et al. ................. 544/316 |
| 8,178,700 B2 | * | 5/2012 | Hedrick ............... C07D 239/10 544/315 |
| 2008/0021029 A1 | * | 1/2008 | Strobel et al. ............. 514/235.8 |
| 2010/0113819 A1 | * | 5/2010 | Belfadhel ............. C07C 263/04 560/24 |
| 2011/0105572 A1 | * | 5/2011 | Watkins et al. ............... 514/357 |
| 2014/0163221 A1 | * | 6/2014 | Gupta .................. C07D 233/34 540/553 |

FOREIGN PATENT DOCUMENTS

EP            476779 A2 *  3/1992
WO    WO-2007056582 A1    5/2007

OTHER PUBLICATIONS

Fujita et al Int. J. Mol. Sci. (2006), 7, pp. 438-450.*
Nomura et al. Ind. Eng. Chem. Res. (1987), 26, pp. 1056-1059.*
International Search Report for PCT/US2012/047310 mailed Sep. 11, 2012.
Schweitzer, "Ethyleneurea I. Synthesis from Urea and Ethylenediamine", Org. Chem., 1950, vol. 15, pp. 471-474.
Schweitzer, "Ethyleneurea. II. Synthesis from Ethylene Glycol or Ethanolamine and Urea (or Carbon Dioxide and Ammonia)", Org. Chem, vol. 15, pp. 475-480.
Fischer et al., "Ueber einige Derivates des Trimethylen- and Aethylendiamins", Annalen, 1886, vol. 232, pp. 227.
Shenoy et al., 2-Imidazolidinones (Ethylene Ureas)—A Review, American Dyestuff Reporter, 1968, pp. 17-34.

* cited by examiner

*Primary Examiner* — Nyeemah A Grazier
(74) *Attorney, Agent, or Firm* — Drinker Biddle & Reath LLP

(57) ABSTRACT

The invention relates to a process for the synthesis of N-substituted cyclic alkylene ureas by reacting a multifunctional aliphatic amine A having at least two amino groups which may be primary or secondary, at least one of which is a primary amino group, $-NH_2$, and at least one of which is a secondary amino group, >NH, the other hydrogen group whereof having been substituted by a hydrocarbyl group which in turn may be substituted by a hydroxyl group, or an amino group, or a carboxyl group, or a ketone carbonyl group, or a hydrazide or hydrazone group, or a mercaptan group, and at least one further functional group selected from the group consisting of primary or secondary amino groups and hydroxyl groups, and an aliphatic organic carbonate component C selected from the group consisting of dialkyl carbonates CD and of alkylene carbonates CA.

25 Claims, No Drawings

PROCESS FOR THE SYNTHESIS OF N-SUBSTITUTED CYCLIC ALKYLENE UREAS

CROSS-REFERENCE TO RELATED APPLICATIONS

This application is a national stage application (under 35 U.S.C. §371) of PCT/US2012/047310, filed Jul. 19, 20126, which claims benefit of European application 11174655.8, filed Jul. 20, 2011.

FIELD OF THE INVENTION

The invention relates to a process for the synthesis of N-substituted cyclic alkylene ureas, and to the products obtained from this process.

BACKGROUND OF THE INVENTION

Various processes to make cyclic alkylene ureas have been described in the literature and in patents, such as in J. Org. Chem. 1950, vol. 15, pages 471 to 474, and 475 to 480, relating to the synthesis of ethylene urea from urea and ethylenediamine, and from ethylene glycol or ethanolamine and urea, or carbon dioxide and ammonia.

As early as 1886, E. Fischer and H. Koch reported in Annalen, vol. 232, page 227 (1886), the preparation of ethylene urea by heating ethylenediamine and diethyl carbonate at 180° C. As described therein, this reaction was carried out in a sealed tube and required the use of high temperature.

In Shenoy, P. K. et al., American Dyestuff Reporter, May 6, 1968, pp. 17 to 34 (352-369), a variety of processes is disclosed for the preparation of ethylene urea (2-imidazolidinone) and derivatives of ethylene urea. At page 18 (353), it is stated that aminoethylethanolamine and urea can be reacted at a temperature of from 100° C. to 180° C. to give N-(2-hydroxyethyl)ethyleneurea. Also, at page 18 (353), it is stated that N-(2-hydroxyethyl)ethyleneurea can be prepared from the reaction of aminoethylethanolamine and diethyl carbonate. At page 19 (354), it is stated that N,N'-(dimethyl) ethyleneurea can be prepared by reacting ethylene urea with formaldehyde followed by catalytic hydrogenation with a nickel catalyst, or by using formaldehyde-formic acid reduction of ethylene urea.

SUMMARY OF THE INVENTION

It has been found in the experiments underlying the present invention that reaction of a multifunctional aliphatic amine having at least two amino groups which may be primary or secondary, at least one of which is a primary amino group, —$NH_2$, and at least one of which is a secondary amino group, >NH, the other hydrogen group whereof having been substituted by a hydrocarbyl group which may be an alkyl or an alkylene or an alkyne group, or an aryl group, having at least one, and preferably not more than twenty carbon atoms, all of which in turn may be substituted by a hydroxyl group, or an amino group, or a carboxyl group, or a ketone carbonyl group, or a hydrazide or hydrazone group, or a mercaptan group, and at least one further functional group selected from the group consisting of primary or secondary amino groups and hydroxyl groups, and a dialkyl carbonate or an alkylene carbonate, preferably in the presence of a basic catalyst, leads to formation of N-substituted cyclic alkylene ureas in a good yield.

The object of the invention is therefore a process for the synthesis of N-substituted cyclic alkylene ureas by reacting a multifunctional aliphatic amine A having at least two amino groups, at least one of which is preferably a primary amino group, —$NH_2$, and at least one of which is preferably a secondary amino group, >NH, the other hydrogen group whereof having been substituted by a hydrocarbyl group which may be an alkyl or an alkylene or an alkyne group, or an aryl group, having at least one, and preferably not more than twenty carbon atoms, all of which in turn may be substituted by a hydroxyl group, or an amino group, or a carboxyl group, or a ketone carbonyl group, or a hydrazide or hydrazone group, or a mercaptan group, and at least one further functional group selected from the group consisting of primary or secondary amino groups and hydroxyl groups, and an aliphatic organic carbonate component C selected from the group consisting of dialkyl carbonates CD and of alkylene carbonates CA, wherein the ratio of the sum n (ps) of the amount of substance it (—$NH_2$) of those primary amino groups —$NH_2$ in the multifunctional amine A which are consumed by formation of a cyclic structure, and of the amount of substance n (>NH) of those secondary amino groups >NH in the multifunctional amine A which are consumed by formation of a cyclic structure, to the sum n(C) of the amount of substance n(CD) of carbonate groups of a dialkyl carbonate CD and the amount of substance n(CA) of carbonate groups in an alkylene carbonate CA, is at least more than 2.

This reaction is preferably conducted in the presence of a basic catalyst selected from the group consisting of alkoxides of alkali metals of group 1 of the Periodical System of Elements, and of alkoxides of earth alkali metals, of group 2 of the Periodical System of Elements, according to recent IUPAC nomenclature, and of mixtures thereof.

A multifunctional amine, in the context of this invention, has at least two amino groups which may be primary or secondary, at least one of which is a primary amino group, —$NH_2$, and at least one of which is a secondary amino group, >NH, the other hydrogen group whereof having been substituted by a hydrocarbyl group which may be an alkyl or an alkylene or an alkyne group, or an aryl group, each having at least one, at least two for an alkylene or alkyne group, or at least five for an aryl group, and preferably not more than twenty carbon atoms, all of which in turn may be substituted by a hydroxyl group, or an amino group, or a carboxyl group, or a ketone carbonyl group, or a hydrazide or hydrazone group, or a mercaptan group, and at least one further functional group selected from the group consisting of primary or secondary amino groups and hydroxyl groups.

DETAILED DESCRIPTION OF THE PREFERRED EMBODIMENTS

The multifunctional amines A are represented by the formula

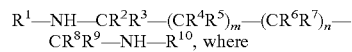

$R^1$—NH—$CR^2R^3$—$(CR^4R^5)_m$—$(CR^6R^7)_n$—$CR^8R^9$—NH—$R^{10}$, where n and m may independently be 0 or 1, and if both m and n are 0, the amine is a derivative of 1,2-diaminoethane, if one of m and n is 1, and the other is 0, the amine is a derivative of 1,3-diaminopropane, and if both m and n are 1, the amine is a derivative of 1,4-diaminobutane, $R^2$ through $R^9$ may be the same or may be different, and are independently selected from the group consisting of a hydrogen atom H, a linear or branched alkyl group having from one to eight carbon atoms, a linear or branched alkyl group having from one to twelve carbon atoms wherein at least one methylene group is replaced by a carbonyl group >C=O, an aryl group, or a halogen atom, i.e. one of F, Cl, Br, and I, an alkoxy group having from one to eight carbon atoms, an aminoalkyl group having from one to eight carbon atoms, an N-alkylaminoalkyl group having a total of from two to sixteen carbon atoms, and a N,N-dialkylaminoalkyl group having a total of from three to twenty-four carbon atoms and a hydroxyalkyl group having from one to eight carbon atoms, $R^4$, $R^5$, $R^6$ and $R^7$ may additionally be a hydroxyl group, —OH, a carboxyl group, —COOH, an amino group, —$NH_2$, or an alkylamino group —$NHR^{11}$, where $R^{11}$ may be a linear, branched or cyclic alkyl group having from one to eight carbon atoms, $R^1$ and $R^{10}$ are independently selected from the group consisting of a hydrogen atom, a linear, branched or cyclic alkyl group having from one to eight carbon atoms, an aryl group, a hydroxyalkyl group —$R^{12}$—OH, and an aminoalkyl group —$R^{13}$—$NHR^{14}$, where $R^{12}$ and $R^{13}$ are independently linear or branched or cyclic alkylene groups having at least two, and up to forty carbon atoms, wherein one or more of the carbon atoms may be separated by an oxygen atom in an ether bond, —C—O—C—, where any two oxygen atoms are preferably separated by two carbon atoms, forming a structure C—O—C—C—O—C—, and where one or more of such oxygen atoms may be replaced by a sulphur atom, or an alkyl- or aryl-substituted nitrogen atom, $R^{14}$ can be a linear, branched or cyclic alkyl group having from one to eight carbon atoms, or a further aminoalkyl group —$R^{15}$—$NHR^{16}$, where $R^{15}$ may independently be selected from the same group as $R^{12}$ and $R^{13}$, and $R^{16}$ may independently be selected from the same group as $R^{14}$, and wherein $R^1$ and $R^{10}$ may not both be a hydrogen atom, and $R^1$ and $R^{10}$ may not both be the same alkyl group.

Preferred are aliphatic linear or branched or cyclic multifunctional amines A having at least two amino groups which may be primary or secondary, at least one of which is a primary amino group, —$NH_2$, and at least one of which is a secondary amino group, >NH, the other hydrogen group whereof having been substituted by a hydrocarbyl group which may be an alkyl or an alkylene or an alkyne group, or an aryl group, each having at least one, at least two for an alkylene or alkyne group, or at least five for an aryl group, and preferably not more than twenty carbon atoms, all of which in turn may be substituted by a hydroxyl group, or an amino group, or a carboxyl group, or a ketone carbonyl group, or a hydrazide or hydrazone group, or a mercaptan group, and at least one further functional group selected from the group consisting of primary or secondary amino groups and hydroxyl groups, and preferably having from two to twenty carbon atoms. Any two amino groups in the same molecule of a multifunctional amine A are separated from each other by at least two successive carbon atoms. One or more of the carbon atoms may be separated by an oxygen atom in an ether bond, —C—O—C—, where any two oxygen atoms are preferably separated by two carbon atoms, forming a structure C—O—C—C—O—C—. One or more of such oxygen atoms may be replaced by a sulphur atom, an alkyl- or aryl-substituted nitrogen atom. It is also possible that the amine A has additional tertiary amino groups. Preferred multifunctional amines A are diethylene triamine(bis-2-aminoethyl-amine), bis-6-aminohexyl-amine, dipropylene triamine(bis-3-aminopropyl-amine), and bis-4-aminobutyl-amine, and preferred amines having four primary or secondary amino groups are triethylenetetramine, N,N'-bis-(2-aminoethyl)-1,3-diaminopropane, and N,N'-bis-(6-aminohexyl)-diaminohexane. It is also possible that the multifunctional amine carries one or more hydroxyl groups, a preferred amine is N-(2-hydroxyethyl)-1,2-diaminoethane.

While multifunctional amines having an even number of amino groups tend to form preferably cyclic reaction products, amines having an odd number of amino groups form aminoalkyl alkylene ureas. The latter are useful intermediates that can be reacted to form carbamate-functional cyclic ureas.

The aliphatic organic carbonate component, C, can be an alkylene carbonate CA, or a dialkyl carbonate, CD, or a mixture of these.

Alkylene carbonates CA are cyclic esters of dihydroxyalkanes preferably having from two to six carbon atoms, such as ethylenecarbonate, 1,2- and 1,3-propylenecarbonate. Useful alkylene carbonates are ethylenecarbonate and 1,2-propylenecarbonate, which are both commercially available.

Dialkyl carbonates CD have the structure $R^a$—O—CO—O—$R^b$, where $R^a$ and Rb may be the same, or may be different, and may independently be selected from the group consisting of linear and branched alkyl radicals having from one to twelve carbon atoms. Especially preferred are dimethyl carbonate, and diethyl carbonate, and mixtures of these.

Basic catalysts which have proved to be useful for the invention are preferably alkali metal or earth alkali metal alkoxides, particularly preferred, lithium methoxide, sodium methoxide and potassium methoxide, or the ethoxides of lithium, sodium, and potassium, and mixtures of these. In a further embodiment, alkali alkoxides or earth alkali alkoxides may be generated in situ, such as from an alkanol and an alkali or earth alkali hydroxide, preferably under removal of water, or by reaction of an alkali or earth alkali metal, their amides, or their hydrides, with an alkanol.

When a multifunctional amine having two primary amino groups and one secondary amino group, such as diethylenetriamine, is used in the reaction with a carbonate compound C, a cyclic urea having an aminoalkyl substituent is formed, in this case, N-(2-aminoethyl)ethylene urea. When a multifunctional amine having three primary amino groups is used, such as tris(aminomethyl)methane, a cyclic urea having an aminoalkyl substituent is formed, in this case, 5-(aminomethyl)propyleneurea. When a multifunctional amine having one primary and one secondary amino group, and an additional hydroxyl group is used, such as N-(2-hydroxyethyl)ethylenediamine, a hydroxyalkyl-alkylene urea is formed, in this case, N-(2-hydroxyethyl)-ethyleneurea. Multifunctional amines having four amino groups, two of which being primary, and two of which being secondary, such as triethylenetetramine, can form reaction products having more than one cyclic urea moiety, in this case, 1,2-ethylene-bis (ethyleneurea-N-yl) having two ethylene urea moieties connected on one of the nitrogen atoms of each moiety by an 1,2-ethylene bridge. Other molecules formed in such reaction are bis-aminoalkyl-functional cyclic ureas, in this case, N,N'-bis(2-aminoethyl)-ethyleneurea. Such N-aminoalkyl-alkylene ureas can form carbamate end groups by reaction with additional organic carbonate C, in this case, N,N'-bis (2-methoxycarbamoylethyl)-ethyleneurea when reacted with dimethyl carbonate, or N,N'-bis(2-(2-hydroxyethyloxy-carbamoyl)-ethyl)-ethyleneurea when reacted with ethylene carbonate.

It has surprisingly been discovered that, depending on the stoichiometry of components A and C, in the case of amines A having three or more amino groups which may be primary or secondary, it is possible to make amino functional cyclic ureas with aminoalkyl substituents on an amide group of the cyclic urea formed, or carbamate functional cyclic ureas with carbamoylalkyl substituents on an amide group of the cyclic urea formed.

This process according to the invention therefore also offers an elegant way to synthesise N-substituted cyclic ureas, having hydroxyalkyl or aminoalkyl or carbamoylalkyl substituents on the amidic nitrogen atoms of the cyclic urea compounds, by reacting the carbonate components C according to the invention with multifunctional amines A having more than two functional groups, preferably three or more primary or secondary amino groups, with at least one primary amino group and at least one secondary amino group, or, in the alternative, multifunctional amines A having two or more primary or secondary amino groups, with at least one primary amino group and at least one secondary amino group, and additionally, at least one hydroxyl group.

If no bicyclic or multicyclic urea compounds are the goal of the synthetical process according to the present invention, it is preferred that the ratio of the sum n (ps) of the amount of substance n (—$NH_2$) of those primary amino groups —$NH_2$ in the multifunctional amine A which are consumed by formation of a cyclic structure, and of the amount of substance n (>NH) of those secondary amino groups >NH in the multifunctional amine A which are consumed by formation of a cyclic structure, to the sum n(C) of the amount of substance n(CD) of carbonate groups of a dialkyl carbonate CD and the amount of substance n(CA) of carbonate groups in an alkylene carbonate CA, is at least 2.2, more preferred, at least 2.4, and particularly preferred, at least 2.5.

Particularly preferred are reactions where
the multifunctional amine A is diethylene triamine, and the product formed is N-(2-aminoethyl)ethyleneurea,
the multifunctional amine A is N-2-hydroxyethyl ethylene diamine, and the product formed is N-(2-hydroxyethyl) ethyleneurea,
the multifunctional amine A is triethylene tetramine, and the product formed is N,N'-bis(2-aminoethyl)ethyleneurea,
the multifunctional amine A is triethylene tetramine, and the product formed is 1,2-ethylidene-bis(imidazolidine-N-yl)
the multifunctional amine A is N,N'-bis-(2-hydroxyethyl) ethylene diamine, and the product formed is N,N'-bis-(2-hydroxyethyl) ethyleneurea,
the multifunctional amine A is N-methyl ethylene diamine, and the product formed is N-methyl ethyleneurea
the multifunctional amine A is diethylene triamine, and the product formed is N-(2-methoxycarbamoyl-ethyl) ethyleneurea, and
the multifunctional amine A is triethylene tetramine, and the product formed is N,N'-bis-(2-methoxycarbamoyl-ethyl)ethyleneurea.

The process according to the invention also makes available a route to synthesise multicyclic alkylene ureas having more than one imidazolidinone or hexahydropyrimidinone moiety from amines that have at least two primary amino groups, and at least two further secondary or primary amino groups which are separated from a primary amino group by two or three of four consecutive carbon atoms. Examples of such amines are triethylenetetramine((N,N'-aminoethyl)-ethylenediamine), 1,2,3,4-tetraaminobutane, 1,2,4,5-tetraaminopentane, 1,2,5,6-tetraaminohexane, 1,3,4,6-tetraaminohexane, 1,3,6,8-tetraaminooctane, N,N'-bis(2-aminoethyl)-cyclohexane-1,4-diamine, and N,N'-bis(2-aminoethyl)-butane-1,4-diamine.

The process according to the invention preferably comprises the following steps:
charging both the amine A and the carbonate C to a reaction vessel,
optionally adding a solvent which is selected from the group consisting of aliphatic linear, branched or cyclic alcohols having from one to eighteen carbon atoms, aliphatic glycols having a linear or branched alkylene chain of from two to six carbon atoms, monoalkyl ethers of any of the preceding alcohols where the alkyl groups have from one to four carbon atoms, monoalkyl ethers or dialkyl ethers of any of the preceding glycols where the alkyl groups have independently from one to four carbon atoms, and of alkyl aromatic compounds, and of mixtures of two or more of any of these,
holding the mixture at a temperature of from 0° C. to 250° C.,
adding the basic catalyst, preferably under stirring,
further holding the reaction mixture at a temperature of from 25° C. to 250° C. during the reaction, and
isolation of the cyclic N-substituted alkylene urea formed.

In a further preferred embodiment, a mixture of solvent, multifunctional amine A, and catalyst is charged into a reactor, and the carbonate component C is added, preferably over a time span of between fifteen minutes and six hours, under mixing conditions such as stirring, or circulating the reaction mixture in a tubular loop which includes at least one mixing section which may be a nozzle set into a tube, or a static mixer. Therefore, another process that can be used comprises the following steps:
charging both the multifunctional amine A and the basic catalyst to a reaction vessel,
optionally adding a solvent which is selected from the group consisting of aliphatic linear, branched or cyclic alcohols having from one to eighteen carbon atoms, aliphatic glycols having a linear or branched alkylene chain of from two to six carbon atoms, monoalkyl ethers of any of the preceding alcohols where the alkyl groups have from one to four carbon atoms, monoalkyl ethers or dialkyl ethers of any of the preceding glycols where the alkyl groups have independently from one to four carbon atoms, and of alkyl aromatic compounds, and of mixtures of two or more of any of these,
holding the mixture at a temperature of from 0° C. to 250° C.,
adding the carbonate component C, preferably under stirring,
further holding the reaction mixture at a temperature of from 25° C. to 250° C. during the reaction, and
isolation of the cyclic N-substituted alkylene urea formed.

If a carbamate functional cyclic alkylene urea is desired, the amount of carbonate can be increased in the initial reaction mixture, or a subsequent step can be added where an amino-functional N-substituted cyclic alkylene urea is reacted with additional carbonate compound to convert the amino-functional N-substituted cyclic alkylene urea to a carbamate-functional N-substituted cyclic alkylene urea.

The multifunctional amine A, the carbonate component C, and the catalyst, may be charged in any order to a reaction vessel. If a solvent is used, it may be charged before addition of the reactants and catalyst, or may be added together with any of these, or may be added last. It is preferred to at least partially replace the air by nitrogen or an other inert gas. The reaction mixture is preferably heated, and continued until the reaction is essentially complete, as evidenced by samples drawn from the reaction mixture. The alcohol released from the carbonate component C, and excess amine A may then be removed, preferably by distillation under reduced pressure. The N-substituted cyclic alkylene urea formed is then isolated.

If a solvent is used, and the N-substituted cyclic alkylene urea is not soluble in the solvent used, the reaction product is preferably isolated as a precipitate by filtration, before or after removal of the excess amine, and the alcohol is preferably removed by distillation under reduced pressure. The precipitate may then be washed with further solvent. If a solvent is used, and the N-substituted cyclic alkylene urea is significantly soluble in the solvent, the N-substituted cyclic alkylene urea may be recovered by partially or completely removing the solvent, or it may be precipitated from the solution by adding a non-solvent, or a combination of both processes. The precipitate may then be washed with further solvent. If no solvent is used, the remaining solids after removing the excess amine and the alcohol by distillation under reduced pressure are washed with one or more of the solvents mentioned.

A substance is called "not soluble" in a specified solvent if it is not significantly soluble in this solvent, at ambient temperature (20° C.). By "not significantly soluble" it is meant that the mass fraction of the substance in question dissolved in a solvent which is in equilibrium with the substance in question is preferably not more than 10%.

If no solvent is used, the remaining solids after removing the excess amine and the alcohol by distillation under reduced pressure are washed with one or more of the solvents mentioned.

The washed precipitate usually has a purity of more than 90%. For further purification, further washing steps, recrystallisation, melt crystallisation, or dissolution of the N-substituted cyclic alkylene urea in water to form a solution which may be purified by ion exchange or adsorption methods can be used. Residual unreacted multifunctional amine can be removed by treatment with ion exchange resins.

The most preferred process is conducted by charging the amine A, the carbonate component C, and the catalyst to a reaction vessel, optionally adding a solvent as detailed infra, optionally, at least partially replacing the air by nitrogen or an other inert gas, and holding the mixture at a reaction temperature of between 0° C. to 250° C. The upper temperature limit is preferably chosen to allow reflux, or support fractional distillation to separate the cyclic urea from reaction byproducts. It is also possible to mix the amine component and the catalyst in the presence of solvent, and add the carbonate component over time according to consumption thereof.

The basic catalyst can be added together with the reactants, or preferably, is slowly added to the mixture of reactants as charged, or to the pre-heated reactants, preferably during a period of between ten minutes and sixty minutes, under stirring. Heating and stirring the reaction mixture is then continued until the reaction has proceeded to essential completion, as shown by the amount of alcohol or diol formed from the carbonate component, C, then separating the excess amine A and alcohol or diol released from the carbonate component C by distillation under reduced pressure, filtering of the residue, and isolating of the N-substituted cyclic alkylene urea formed.

In a variant, a solvent can be added to the reactants, which solvent is selected from the group consisting of aliphatic linear, branched or cyclic alcohols having from one to eighteen carbon atoms, aliphatic glycols having a linear or branched alkylene chain of from two to six carbon atoms, monoalkyl ethers of any of the preceding alcohols where the alkyl groups have from one to four carbon atoms, monoalkyl ethers or dialkyl ethers of any of the preceding glycols where the alkyl groups have independently from one to four carbon atoms, and of alkyl aromatic compounds, and of mixtures of two or more of any of these. The solvent is chosen to be inert under the reaction conditions, i.e., so that is does not react with any of the starting materials, or with the desired end product.

In one approach, the excess multifunctional amine A and the alcohol formed in the reaction is removed by, e.g., distillation under reduced pressure. Upon cooling, the N-substituted cyclic alkylene urea usually solidifies, or separates from the solvent if a solvent is present. Such solvent is chosen to dissolve the N-substituted cyclic alkylene urea only slightly or not at all. It is also possible to separate the N-substituted cyclic alkylene urea from the unreacted amine and the alcohol formed, by filtration from the reaction mixture after cooling if it forms a solid. Aliphatic ethers like dimethoxyethane or alkyl aromatic compounds such as toluene or xylene or mixtures of these optionally with mesitylene and cumene which are sold as "solvent naphtha" are particularly suitable. Isolation is then best effected by filtration, in the case of solid products, which leaves the solid N-substituted cyclic alkylene urea which is only sparingly soluble in the said solvents. Ketones which cannot be used during the reaction as solvents, like acetone and methyl isobutyl ketone, have been found useful when washing the isolated N-substituted cyclic alkylene urea.

An important advantage of the process claimed is the essential absence of water in the reaction which leads to the low level of water in the final product. In the case where the N-substituted cyclic alkylene urea is solid at ambient temperature (20° C.), this process allows to obtain the cyclic urea as a free-flowing solid, and also, in the form of free-flowing prills, with little or no propensity to form aggregates. The mass fraction of water in the product as isolated from the process is not more than 5%, and is preferably found to be not more than 1%.

The invention is further illustrated by the following examples which are not intended to be limiting.

The following analytical tools were used:

$^{13}$C-NMR: Samples were dissolved in $D_2O$ for analysis as solutions having a mass fraction of solute of 10%. The NMR spectra were acquired on a Bruker Avance II 400 NMR spectrometer using a 10 mm PABBO probe with the "quant2_45" method with the D1 delay increased from 10 s to 30 s to give better quantitation for the carbonyl peaks.

GC/MS Conditions: samples were dissolved in acetonitrile to make solutions having a mass fraction of solute of 0.5%. The injection port temperature was 225° C., the column temperature was initially 175° C., rising by 20 K/min until 200° C. was reached. A constant helium flow of 1 mL/min was used.

FTIR: Infrared spectra were acquired using a DuraScope single reflection diamond ATR accessory mounted in the sample chamber of a Digilab 7000e FTIR spectrometer.

EXAMPLES

In these examples, and also in the remaining specification, the following definitions apply:

"Purity" is the ratio of the mass of the desired product to the mass of the material used (when used as starting material) or obtained (when present in the reaction product), usually measured in "%", or cg/g.

"Strength" is the mass fraction $w_B$ of solute B in a solution S, calculated as the ratio of the mass $m_B$ of solute B and the mass $m_S$ of the solution, usually measured in "%", or cg/g.

Yield is the ratio of the mass of the desired reaction product obtained in a chemical reaction or a physicochemical process, and the expected mass of the reaction product without any loss due to side reactions or lost product during isolation thereof.

Example 1

A product was prepared by the following procedure according to the invention:

165.0 g (1.6 mol) of diethylenetriamine having a purity of 99.5% and 45.45 g (0.5 mol) of dimethyl carbonate having a purity of 99%, and 10.8 g (0.05 mol) of a 25% strength solution of sodium methoxide in methanol were charged to a reaction vessel under a nitrogen purge and mixed at room temperature (23° C.). An exotherm was observed and the reaction mixture was kept under cooling at a temperature not exceeding 55° C. After one hour of mixing, the temperature was gradually increased 90° C. and held for one hour, the temperature was increased to 120° C. and held for two hours. The resulting product was analysed by $^{13}$C-NMR and IR and found to be predominantly N-(2-aminoethyl)-ethylene urea, together with a minor amount of unreacted diethylenetriamine. Carbamate groups were not found in this reaction product.

Example 2

Two-Step Formation of a Carbamate

A product was prepared by the following procedure according to the invention:

52.02 g (0.5 mol) of diethylenetriamine having a purity of 99.5%, 40.09 g (0.45 mol) of dimethylcarbonate having a purity of 99%, 28 g of toluene, and 9.0 g (0.05 mol) of a 30% strength solution of sodium methoxide in methanol were charged to a reaction vessel under nitrogen purge and mixed at room temperature (23° C.). An exotherm was observed, the reaction mixture was kept under stirring and cooling at a temperature not exceeding 55° C. After one hour, the temperature was increased to 90° C. and held for one hour, then the temperature was increased to 120° C. and held for two hours. The resulting product predominantly consisted of N-(2-aminoethyl)-ethyleneurea.

In a subsequent reaction step, additional 42 g (0.47 mol) of dimethylcarbonate having a purity of 99% were charged to the above reaction vessel, the resultant mixture was slowly heated to 90° C. and held for four hours. The solvent and methanol were removed by distillation under reduced pressure. This resulting product was analysed by $^{13}$C-NMR and IR and found to predominantly consist of N-(2-methoxycarbamoylethyl)-ethyleneurea.

Example 3

Formation of a Carbamate 133.03 g (1.03 mol) of N-(2-aminoethyl)-ethyleneurea having a purity of 96%, 81.82 g (0.91 mol) of dimethylcarbonate having a purity of 99%, and 9.0 g (0.05 mol) of a 30% strength solution of sodium methoxide in methanol were charged to a reaction vessel under nitrogen purge and mixed at room temperature (23° C.). An exotherm was observed, the reaction mixture was kept under stirring and cooling at a temperature not exceeding 45° C. After one hour, the temperature was increased to 50° C. and held for one hour whereupon the reaction mixture solidified. The resulting product was analysed by $^{13}$C-NMR and found to predominantly consist of N-(2-methoxycarbamoylethyl)-ethyleneurea.

Example 4

A product was prepared by the following procedure according to the invention:

52.52 g (0.5 mol) of N-(2-hydroxyethyl)-ethylenediamine having a purity of 99%, 40.09 g (0.45 mol) of dimethylcarbonate having a purity of 99%, and 9.0 g (0.05 mol) of a 30% strength solution of sodium methoxide in methanol were charged to a reaction vessel under nitrogen purge and mixed at room temperature (23° C.). An exotherm was observed, and the temperature was kept by cooling below 55° C. The temperature was then slowly increased to 90° C. and held for four hours. The temperature was then slowly increased to 90° C. and held for four hours. The resulting crude product was found to predominantly consist of N-(2-hydroxyethyl)-ethyleneurea.

Example 5

Formation of a Dicyclic Urea

A product was prepared by the following procedure according to the invention:

88.2 g (0.6 mol) of triethylenetetramine having a purity of 99.5%, 94.6 g (1.05 mol) of dimethylcarbonate having a purity of 99%, 28 g of toluene, and 18.0 g (0.1 mol) of a 30% strength solution of sodium methoxide in methanol were charged to a reaction vessel under nitrogen purge and mixed at room temperature (23° C.). An exotherm was observed, the reaction mixture was kept under stirring and cooling at a temperature not exceeding 55° C. After one hour, the temperature was increased to 90° C. and held for one hour, then the temperature was increased to 120° C. and held for two hours. The resulting product predominantly consisted of 1,2-ethylidene bis(imidazolidine-N-yl) of formula

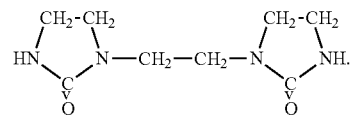

Example 6

Formation of N-Alkyl Ethyleneurea

A product was prepared by the following procedure according to the invention:

78.0 g (1.0 mol) of N-methyl ethylenediamine having a purity of 95%, 22.7 g (0.25 mol) of dimethylcarbonate having a purity of 99%, and 10.8 g (0.05 mol) of a 25% strength solution of sodium methoxide in methanol were charged to a reaction vessel under nitrogen purge and mixed at room temperature (23° C.). An exotherm was observed, and the temperature was kept by cooling below 55° C. The temperature was then slowly increased to 90° C. and held for four hours. The temperature was then slowly increased to 90° C. and held for four hours. The resulting crude product was found to predominantly consist of N-methyl ethyleneurea.

The invention claimed is:

1. A process for the synthesis of an N-substituted cyclic alkylene urea comprising reacting in the presence of a basic catalyst, a multifunctional aliphatic amine A having
   at least two amino groups,
   wherein at least one of the at least two amino groups is a primary amino group, —NH$_2$, and at least one of the at least two amino groups is a secondary amino group, >NH, the other hydrogen group whereof having been substituted by a hydrocarbyl group, and
   an aliphatic organic carbonate component C selected from the group consisting of dialkyl carbonates CD, alkylene carbonates CA, and combinations thereof,
   wherein the ratio of the sum n(ps) of the amount of a substance n(-NH$_2$) of the primary amino groups —NH$_2$ in the multifunctional aliphatic amine A which are consumed by formation of a cyclic structure, and of the amount of a substance n(>NH) of those secondary amino groups >NH in the multifunctional aliphatic amine A which are consumed by formation of a cyclic structure, to the sum n(C) of the amount of substance n(CD) of carbonate groups of the dialkyl carbonate CD and the amount of substance n(CA) of carbonate groups in the alkylene carbonate CA, is more than 2.

2. The process of claim 1, wherein the hydrocarbyl group is an alkyl, alkylene, alkyne or an aryl group, and wherein the hydrocarbyl group has at least one carbon atom which may be substituted by a hydroxyl group, an amino group, a carboxyl group, a ketone carbonyl group, a hydrazide group, a hydrazone group, or a mercaptan group.

3. The process of claim 1, wherein the process is conducted in the presence of a basic catalyst selected from the group consisting of alkoxides of alkali metals of group 1 of the Periodic Table of the Elements, and of alkoxides of alkaline earth metals of group 2 of the Periodic Table of the Elements.

4. The process of claim 1, wherein the multifunctional aliphatic amine A is represented by the formula

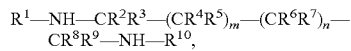

R$^1$—NH—CR$^2$R$^3$—(CR$^4$R$^5$)$_m$—(CR$^6$R$^7$)$_n$—CR$^8$R$^9$—NH—R$^{10}$, wherein n and m may independently be 0 or 1, and wherein
   if both m and n are 0, the amine is a derivative of 1,2-diaminoethane,
   if one of m and n is 1, and the other is 0, the amine is a derivative of 1,3-diaminopropane, and
   if both m and n are 1, the amine is a derivative of 1,4-diaminobutane,
R$^2$ through R$^9$ may be the same or may be different, and are independently selected from the group consisting of a hydrogen atom H, a linear or branched alkyl group having from one to eight carbon atoms, a linear or branched alkyl group having from one to twelve carbon atoms wherein at least one methylene group is replaced by a carbonyl group >C=O, an aryl group, or a halogen atom, an alkoxy group having from one to eight carbon atoms, an aminoalkyl group having from one to eight carbon atoms, an N-alkylaminoalkyl group having a total of from two to sixteen carbon atoms, and a N,N-dialkylaminoalkyl group having a total of from three to twenty-four carbon atoms and a hydroxyalkyl group having from one to eight carbon atoms,
R$^4$, R$^5$, R$^6$ and R$^7$ may additionally be a hydroxyl group —OH, a carboxyl group —COOH, an amino group —NH$_2$, or an alkylamino group —NHR$^{11}$, where R$^{11}$ may be a linear, branched or cyclic alkyl group having from one to eight carbon atoms,
R$^1$ and R$^{10}$ are independently selected from the group consisting of a hydrogen atom, a linear, branched or cyclic alkyl group which may be saturated, having from one to eight carbon atoms, an aryl group, a hydroxyalkyl group —R$^{12}$—OH, and an aminoalkyl group —R$^{13}$—NHR$^{14}$, where R$^{12}$ and R$^{13}$ are independently linear or branched or cyclic alkylene groups having at least two, and up to forty carbon atoms, wherein one or more of the carbon atoms may be separated by an oxygen atom in an ether bond, —C—O—C—, where any two oxygen atoms may be separated by two carbon atoms, forming a structure C—O—C—C—O—C—, and where one or more of such oxygen atoms may be replaced by a sulphur atom, or an alkyl- or aryl-substituted nitrogen atom, R$^{14}$ can be a linear, branched or cyclic alkyl group having from one to eight carbon atoms, or a further aminoalkyl group —R$^{15}$—NHR$^{16}$, where R$^{15}$ may independently be selected from the same group as R$^{12}$ and R$^{13}$, and R$^{16}$ may independently be selected from the same group as R$^{14}$, and wherein R$^1$ and R$^{10}$ may not both be a hydrogen atom, and R$^1$ and R$^0$ may not both be the same alkyl group.

5. The process of claim 1, wherein the multifunctional aliphatic amine A has at least two amino groups which may be primary or secondary, wherein at least one of the amino groups is a primary amino group and at least one of the amino groups is a secondary amino group, and at least one further functional group selected from the group consisting of primary amino groups, secondary amino groups, and hydroxyl groups.

6. The process of claim 1, wherein the carbonate component C comprises a dialkyl carbonate CD having the structure R$^a$—O—CO—O—R$^b$, where R$^a$ and R$^b$ are the same or different and are independently selected from the group consisting of linear and branched alkyl radicals having from one to twelve carbon atoms.

7. The process of claim 6, wherein the dialkyl carbonate CD is selected from the group consisting of dimethyl carbonate, diethyl carbonate, and mixtures of dimethyl carbonate and diethyl carbonate.

8. The process of claim 1, wherein the carbonate component C comprises alkylene carbonates CA having an alkylene group of from two to six carbon atoms.

9. The process of claim 8 wherein the alkylene carbonate is selected from the group consisting of ethylene carbonate and 1,2-propylene carbonate.

10. The process of claim 1, wherein the basic catalyst is an alkali metal alkoxide selected from the group consisting of lithium methoxide, lithium ethoxide, sodium methoxide, sodium ethoxide, potassium methoxide, potassium ethoxide, and mixtures of lithium methoxide, lithium ethoxide, sodium methoxide, sodium ethoxide, potassium methoxide, and potassium ethoxide.

11. The process of claim 1, wherein the alkoxides are generated in situ.

12. The process of claim 11, wherein the alkoxides are generated by reacting an alkanol, and a compound selected from the group consisting of an alkali hydroxide, an alkali hydride, an alkali amide, an alkaline earth hydroxide, an alkaline earth hydride, and an alkaline earth amide.

13. The process of claim 1, further comprising the following steps:

charging both the multifunctional aliphatic amine A and the carbonate component C to a reaction vessel, optionally adding a solvent which is selected from the group consisting of aliphatic linear, branched or cyclic alcohols having from one to eighteen carbon atoms, aliphatic glycols having a linear or branched alkylene chain of from two to six carbon atoms, monoalkyl ethers of aliphatic linear, branched or cyclic alcohols having from one to eighteen carbon atoms where the alkyl groups have from one to four carbon atoms, monoalkyl ethers or dialkyl ethers of aliphatic glycols having a linear or branched alkylene chain of from two to six carbon atoms where the alkyl groups have independently from one to four carbon atoms, alkyl aromatic compounds, and of mixtures of two or more of any of these, holding the mixture at a temperature of from 0° C. to 250° C., adding the basic catalyst, optionally with stirring, further holding the reaction mixture at a temperature of from 25° C. to 250° C. during the reaction, and isolating the cyclic N-substituted alkylene urea formed.

14. The process of claim 1 further comprising the following steps:

charging both the multifunctional aliphatic amine A and the basic catalyst to a reaction vessel, optionally adding a solvent which is selected from the group consisting of aliphatic linear, branched or cyclic alcohols having from one to eighteen carbon atoms, aliphatic glycols having a linear or branched alkylene chain of from two to six carbon atoms, monoalkyl ethers of aliphatic linear, branched or cyclic alcohols having from one to eighteen carbon atoms where the alkyl groups have from one to four carbon atoms, monoalkyl ethers or dialkyl ethers of aliphatic glycols having a linear or branched alkylene chain of from two to six carbon atoms where the alkyl groups have independently from one to four carbon atoms, alkyl aromatic compounds, and of mixtures of two or more of any of these, holding the mixture at a temperature of from 0° C. to 250° C., adding the carbonate component C, optionally with stirring, further holding the reaction mixture at a temperature of from 25° C. to 250° C. during the reaction, and isolating the cyclic N-substituted alkylene urea formed.

15. The N-substituted cyclic alkylene urea obtained by the process of claim 1, wherein the N-substituted cyclic alkylene urea isolated from the process has a mass fraction of water of less than 5%.

16. The process of claim 1, wherein the multifunctional aliphatic amine A is selected from the group consisting of bis-(2-aminoethyl)-amine, bis-(6-aminohexyl)-amine, bis-(3-aminopropyl)-amine, bis-(4-aminobutyl)-amine, N,N'-bis(2-aminoethyl)-ethylenediamine, N,N'-bis-(2-aminoethyl)-1,3-diaminopropane, N,N'-bis-(6-aminohexyl)-diaminohexane, and N-(2-hydroxyethyl)-1,2-diaminoethane.

17. The process of claim 1, wherein the N-substituted cyclic alkylene urea is synthesised by reacting the carbonate component C with a multifunctional aliphatic amine A having four or more amino groups selected from primary and secondary amino groups, at least one of which is a primary amino group.

18. The process of claim 1, wherein the multifunctional aliphatic amine A is diethylene triamine and the product formed is N-(2-aminoethyl) ethyleneurea.

19. The process of claim 1, wherein the multifunctional aliphatic amine A is N-2-hydroxyethyl ethylene diamine, and the product formed is N-(2-hydroxyethyl) ethyleneurea.

20. The process of claim 1, wherein the multifunctional aliphatic amine A is triethylene tetramine, and the product formed is N,N'-bis(2-aminoethyl) ethyleneurea.

21. The process of claim 1, wherein the multifunctional aliphatic amine A is triethylene tetramine, and the product formed is 1,2-ethylidene-bis(imidazolidine-N-yl).

22. The process of claim 1, wherein the multifunctional aliphatic amine A is N-methyl ethylene diamine, and the product formed is N-methyl ethyleneurea.

23. The process of claim 1, wherein the multifunctional aliphatic amine A is diethylene triamine, and the product formed is N-(2-methoxycarbamoyl-ethyl) ethyleneurea.

24. The process of claim 1, wherein the N-substituted cyclic alkylene urea is in the form of a free flowing solid.

25. The process of claim 1, wherein the reacting is conducted at temperatures between 90 and 120° C.

* * * * *